(12) United States Patent  
Wang et al.

(10) Patent No.: US 7,792,344 B2
(45) Date of Patent: Sep. 7, 2010

(54) IMAGE CAPTURE CONTROL FOR IN VIVO AUTONOMOUS CAMERA

(75) Inventors: Kang-Huai Wang, Saratoga, CA (US); Tong Wu, Fremont, CA (US)

(73) Assignee: Capso Vision Inc., Saratoga, CA (US)

( * ) Notice: Subject to any disclaimer, the term of this patent is extended or adjusted under 35 U.S.C. 154(b) by 0 days.

(21) Appl. No.: 12/543,508

(22) Filed: Aug. 19, 2009

(65) Prior Publication Data

US 2009/0322865 A1 Dec. 31, 2009

Related U.S. Application Data

(63) Continuation-in-part of application No. 11/533,304, filed on Sep. 19, 2006.

(51) Int. Cl.
*G06K 9/00* (2006.01)
(52) U.S. Cl. .................. 382/128; 382/236; 348/699; 348/700
(58) Field of Classification Search .................. 382/128
See application file for complete search history.

(56) References Cited

U.S. PATENT DOCUMENTS

| 4,278,077 | A |   | 7/1981 | Mizumoto |
| 5,581,302 | A | * | 12/1996 | Ran et al. ............... 375/240.16 |
| 5,588,067 | A | * | 12/1996 | Peterson et al. ............. 382/103 |
| 5,604,531 | A |   | 2/1997 | Idann et al. |
| 6,428,469 | B1 |  | 8/2002 | Idann et al. |
| 6,480,225 | B1 | * | 11/2002 | Kim ........................... 348/143 |
| 6,709,387 | B1 | * | 3/2004 | Glukhovsky et al. ........ 600/109 |
| 6,800,060 | B2 | * | 10/2004 | Marshall ..................... 600/309 |
| 6,803,945 | B1 | * | 10/2004 | Needham .................. 348/207.1 |
| 6,936,003 | B2 | * | 8/2005 | Iddan .......................... 600/114 |
| 6,939,292 | B2 | * | 9/2005 | Mizuno ....................... 600/118 |
| 7,271,830 | B2 | * | 9/2007 | Robins et al. ............. 348/208.6 |
| 7,492,935 | B2 | * | 2/2009 | Glukhovsky ............... 382/128 |
| 7,643,056 | B2 | * | 1/2010 | Silsby ........................ 348/155 |
| 2003/0023150 | A1 | * | 1/2003 | Yokoi et al. ................. 600/300 |
| 2003/0202605 | A1 | * | 10/2003 | Hazra et al. ............. 375/240.26 |
| 2005/0143624 | A1 | * | 6/2005 | Iddan .......................... 600/112 |
| 2006/0293558 | A1 | * | 12/2006 | De Groen et al. ........... 600/101 |
| 2007/0098379 | A1 | * | 5/2007 | Wang et al. ................... 396/14 |
| 2007/0116119 | A1 | * | 5/2007 | Wang ...................... 375/240.12 |
| 2009/0299359 | A1 | * | 12/2009 | Swain .......................... 606/27 |
| 2009/0322865 | A1 | * | 12/2009 | Wang et al. ................... 348/68 |

* cited by examiner

*Primary Examiner*—Sath V. Perungavoor
(74) *Attorney, Agent, or Firm*—Blairtech Solution LLC

(57) ABSTRACT

Systems and methods are provided for motion detection and capture control of video data from a capsule camera system having an on-board storage. The capsule camera system moves through the GI tract under the action of peristalsis and records images of the intestinal walls. The capsule's movement is episodic and jerky. The capacity of the on-board storage is limited. In order to avoid unnecessary capture of images when the capsule camera moves very slowly or stalls, motion detection technique is utilized to help control image capture. Furthermore, an adaptive capture control is disclosed that automatically adjusts the threshold level of capture control to maintain proper image capture. The invented capture control also conserves precious battery power by eliminating capture of unnecessary images when the capsule camera moves too slowly or stalls. The present invention of image capture control and threshold update is also applicable to a capsule camera system having a wireless transmitter instead of an on-board storage.

35 Claims, 14 Drawing Sheets

IMAGE CAPTURE CONTROL FOR IN VIVO AUTONOMOUS CAMERA

CROSS REFERENCE TO RELATED APPLICATIONS

The present invention is related and claims priority to U.S. patent application, entitled "IN VIVO AUTONOMOUS CAMERA WITH ON-BOARD DATA STORAGE OR DIGITAL WIRELESS TRANSMISSION IN REGULATORY APPROVED BAND", Ser. No. 11/533,304, filed on Sep. 19, 2006. The U.S. Non-Provisional Patent Application is hereby incorporated by reference in its entireties.

FIELD OF THE INVENTION

The present invention relates to diagnostic imaging inside the human body. In particular, the present invention relates to controlling image capture of capsule camera having on-board storage or wireless transmission.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An early example of a camera in a swallowable capsule is described in U.S. Pat. No. 5,604,531. Other patents, such as U.S. Pat. Nos. 6,709,387 and 6,428,469, describe more details of such a system, using a transmitter to send the camera images to an external receiver. Still other patents, including U.S. Pat. No. 4,278,077, describe similar technologies. For example, U.S. Pat. No. 4,278,077 shows a capsule with a camera for the stomach, which includes film in the camera. U.S. Pat. No. 6,939,292 shows a capsule with a buffering memory, a timer, and a transmitter.

An autonomous capsule camera system with on-board data storage was disclosed in the U.S. patent application Ser. No. 11/533,304, entitled "In Vivo Autonomous Camera with On-Board Data Storage or Digital Wireless Transmission in Regulatory Approved Band," filed on Sep. 19, 2006. This application describes a motion detection is conducted using a portion of each image, the portion being stored in a partial frame buffer. In one embodiment, two partial frame buffers are used as an operand buffers for a reduced version of a current image and a reference image, respectively. The reference frame buffer corresponds to the one containing a previously stored or transmitted digital image. When the image in the operand partial frame buffer is determined not to be stored, that partial frame buffer may be overwritten by the next digital image to be motion-detected. Otherwise, the operand partial frame buffer would be designated the next reference partial frame buffer, and the current reference partial frame buffer is designated the next operand partial frame buffers. In the above application, a metric for measuring the degree of motion between the two partial images described and is used to compare with a threshold as to whether to capture an underlying image or as to determine a proper compression ratio for the underlying image.

While the motion detection has greatly helped to eliminate some unnecessary image capture and conserved the precious on-board storage and battery power, it may not fully address dynamic environmental issue. The environment in the small intestine and that in the colon may present very different imaging environment. The small intestine has a smaller average diameter than the colon. Therefore, the distance between the capsule camera and a non-contacting lumen wall being imaged is closer for the small intestine than the colon. The degree of motion resulted from a movement in the small intestine may be different from that in the colon. Furthermore, the capsule camera may experience different rate of transit in the small intestine and the colon. The effect of transit rate may also need to be taken into consideration for image capture. It is the goal of the present invention to address the need for an adaptive and dynamic method to manage and control image capture.

BRIEF SUMMARY OF THE INVENTION

The present invention provides an adaptive and dynamic method to adjust the parameter for image capture of a capsule camera with on-board image storage or wireless transmitter. A metric measuring the degree of motion is first computed from a partial frame of current image and a partial frame of a previously capture image. The metric is then compared against a set of parameters to determine a proper action for the underlying image. In a simplest case, the metric is a scalar (one-dimensional data) and the metric is compared against a single threshold to determine if a motion is detected.

For the intended in vivo autonomous camera application, the battery power is limited and low-power processing is required. Accordingly, the metrics that require low power consumption are preferred embodiment in the present invention. Nevertheless, the present invention is not limited to the metric requiring low-power. In one embodiment, the variance of difference of corresponding pixel values of partial frames for a current image and a previously capture image is used as the metric. In another embodiment, a count of zero-motion vectors is relied on as the metric where the zero-motion is measured between corresponding blocks between partial frames of a current image and a previously captured image. In yet another embodiment, the centers of mass of partial frames of a current image and a previously captured image are computed and the metric is a measurement of the difference between the two centers of mass.

Due to the environmental differences in GI tract, the measured metric value may be different for the same amount of motion. In order to automatically adjust capture control so that the capture of images will occur at roughly the same amount of motion, a method of automatic adjustment of the threshold for image capture is invented and described. In one embodiment, the average number of skipped images is tracked and monitored. When the capture control determines to capture an underlying image, the average number of skipped images is updated accordingly. The threshold and average skipped frames are then evaluated for threshold adjustment. If the average number of skipped images is smaller than a low limit and the threshold has not reached a maximum value, the threshold is increased. If the average number of skipped images is larger than a high limit and the threshold has not reached a minimum threshold, the threshold is decreased.

The present invention can also be applied to a capsule camera system using a wireless transmitter instead of on-board storage. The capture control for the capsule camera system having a wireless transmitter is substantially the same as that for the capsule camera system having on-board storage. For such capsule camera system, when motion detection is asserted, an underlying image is transmitted via the wireless transmitter to an external base station instead of storing in the on-board storage.

The foregoing and other objects, features and advantages of the present invention will be apparent from the following detailed description of the preferred embodiments which make reference to several figures of the drawing.

DETAILED DESCRIPTION OF THE INVENTION

Today, semiconductor memories are low-cost, low-power, easily available from multiple sources, and compatible with application specific integrated circuit (ASIC) and sensor electronics (i.e., the data sources), and a personal computer (i.e., the data destination) without format conversion devices. One embodiment of the present invention allows images to be stored in an "on-board storage" using merchant semiconductor memories (i.e., "off-the-shelf" memories, or memories manufactured using industry standard memory processes, or readily available memory processes). To enable taking a large number of diagnostic images in such areas as the colon, a method of the present invention controls the number of images stored in the semiconductor memories by detecting camera movements. One embodiment of the present invention takes advantage of the fact that, for much of the time, either the capsule does not move in the GI tract, or the portion of the GI tract within the camera's view is not changing. For such periods of time, the images need not be stored. In this disclosure the terms "capsule" and "capsule camera" are inter-exchangeable. Also the terms "capsule system" and "capsule camera system" are inter-exchangeable.

According to another aspect of the present invention, a specialized frame buffer is provided. As a 640×480 resolution VGA-type image has 300,000 pixels, and if each such pixel is represented equally by one byte of data (e.g., 8 bits), the image requires a 2.4 M-bit frame buffer ("regular frame buffer"). Because of its physical and power constraints, in practice, a capsule camera can provide only a fraction of the regular frame buffer. One embodiment of the present invention provides, therefore, a highly efficiency image compression algorithm to reduce the storage requirement, taking into consideration the limited processing power and limited memory size available in the capsule. In one embodiment, one or more "partial frame buffers" are provided, with each partial frame buffer being significantly smaller than a regular frame buffer. As the per-bit size in memory circuits continues to decrease, a method of the present invention may use the larger memory size made possible to achieve greater sensor resolution.

Figure 1A:
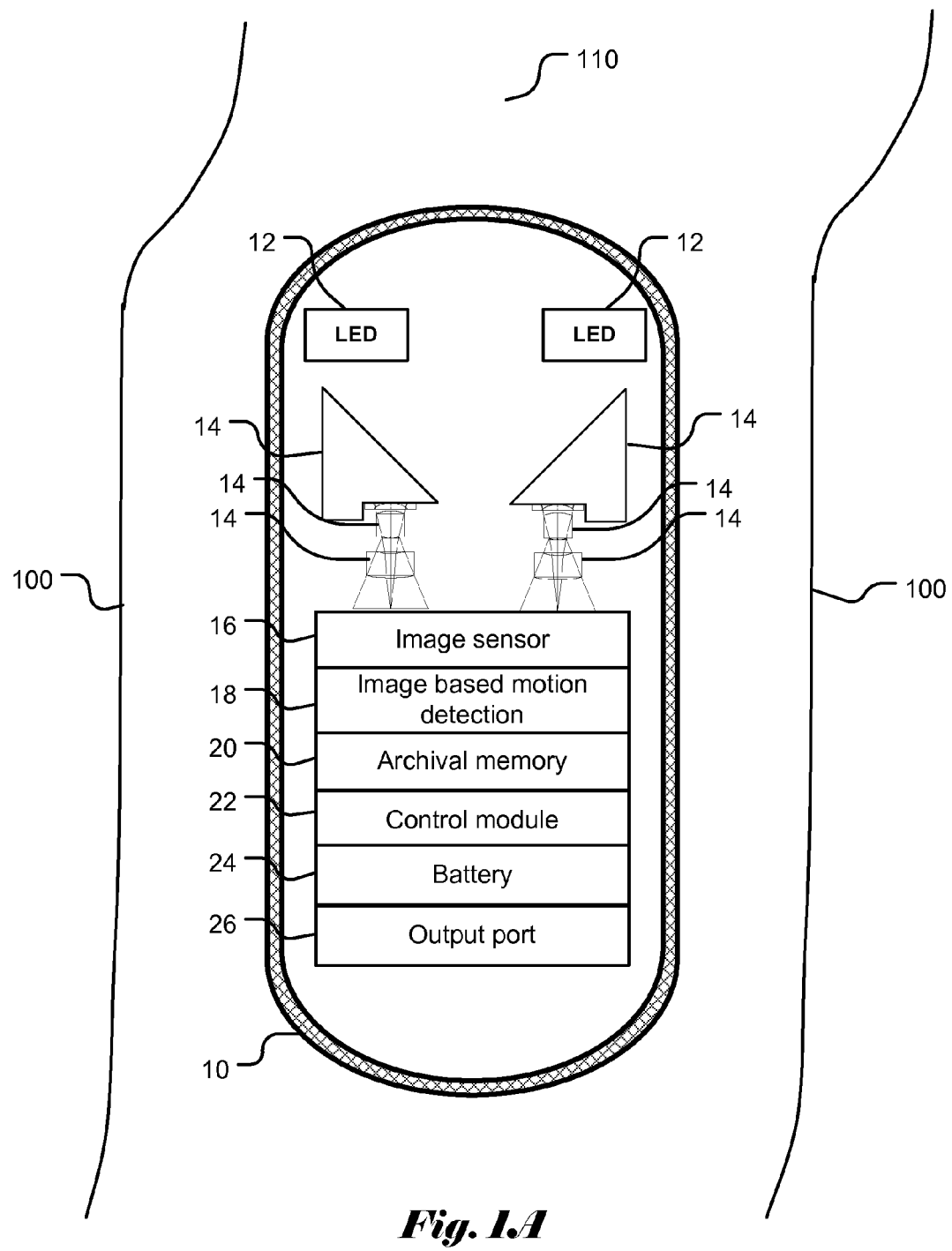
FIG. 1A shows schematically capsule camera system having on-board storage, according to one embodiment of the present invention, where the capsule camera shown is inside the GI tract.

FIG. 1A shows a swallowable capsule system 110 inside body lumen 100, in accordance with one embodiment of the present invention. Lumen 100 may be, for example, the colon, small intestines, the esophagus, or the stomach. Capsule system 110 is entirely autonomous while inside the body, with all of its elements encapsulated in a capsule housing 10 that provides a moisture barrier, protecting the internal components from bodily fluids. Capsule housing 10 is transparent, so as to allow light from the light-emitting diodes (LEDs) of illuminating system 12 to pass through the wall of capsule housing 10 to the lumen 100 walls, and to allow the scattered light from the lumen 100 walls to be collected and imaged within the capsule. Capsule housing 10 also protects lumen 100 from direct contact with the foreign material inside capsule housing 10. Capsule housing 10 is provided a shape that enables it to be swallowed easily and later to pass through of the GI tract. Generally, capsule housing 10 is sterile, made of non-toxic material, and is sufficiently smooth to minimize the chance of lodging within the lumen.

As shown in FIG. 1A, capsule system 110 includes illuminating system 12 and a camera that includes optical system 14 and image sensor 16. An image captured by image sensor 16 may be processed by image-based motion detector 18, which determines whether the capsule is moving relative to the portion of the GI tract within the optical view of the camera. Image-based motion detector 18 may be implemented in software that runs on a digital signal processor (DSP) or a central processing unit (CPU), in dedicated hardware, or a combination of both software and hardware. Image-based motion detector 18 may have one or more partial frame buffers. A semiconductor nonvolatile archival memory 20 may be provided to allow the images to be retrieved at a docking station outside the body, after the capsule is recovered. System 110 includes battery power supply 24 and an output port 26. Capsule system 110 may be propelled through the GI tract by peristalsis.

Illuminating system 12 may be implemented by LEDs. In FIG. 1, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. One function of control module 22 is to control the LEDs during image capture operation.

Motion detection module 18 selects an image to retain when the image shows enough motion relative to the previous image in order to save the limited storage space available. The images are stored in an on-board archival memory system 20. The output port 26 shown in FIG. 1A is not operational in vivo but uploads data to a work station after the capsule is recovered, having passed from the body. Motion detection can also be used to regulate the image capture rate (i.e., the frequency at which the camera captures an image). It is desirable to increase the capture rate when the capsule is in motion. If capsule remains at the same place, it may be desirable to capture an image less frequently to save battery power. The details of the motion detector will be described in respective embodiments of the present invention.

The motion detector comprises a module that computes a metric of motion. Depending the amount of motion as indicated by the metric, the motion detector will determine if the underlying image should be captured, i.e., stored in the on-board storage. If the amount of motion is small so that the differences between the underlying image and a previously captured image are small, the underlying image may not be needed to store, i.e., the underlying is not captured. The previously captured image is also called a reference image and the image not captured is also referred to as a skipped image in this specification. As will be discussed later, the amount of motion as measured by the metric is different for different diameters of the GI tract sections.

Figure 1B:
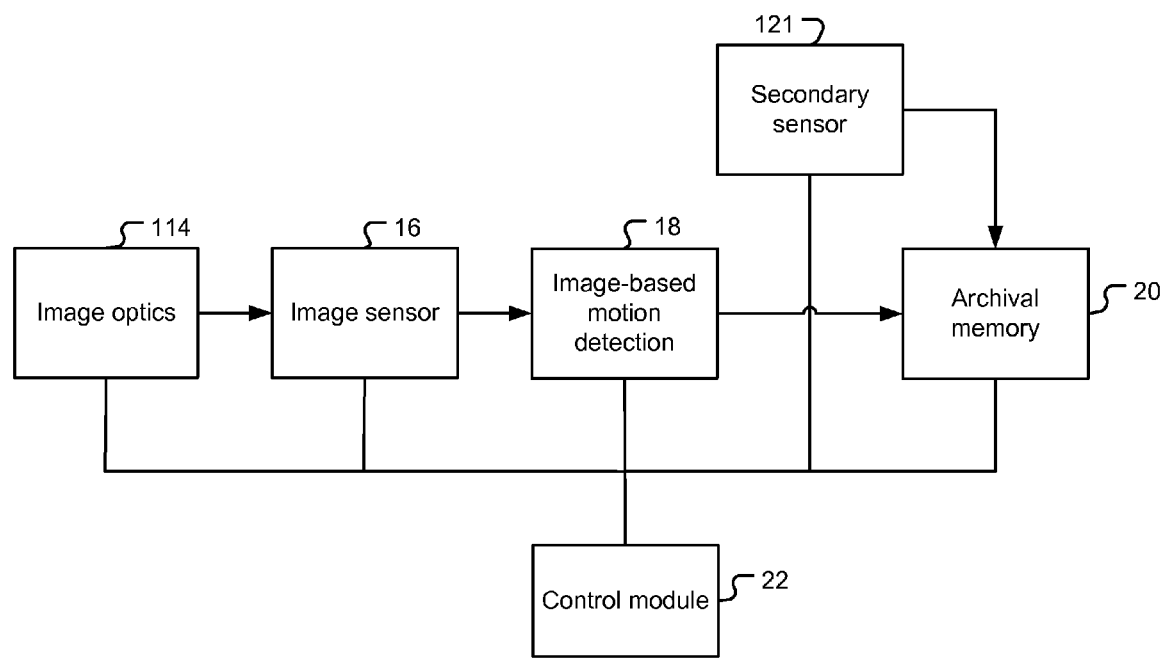
FIG. 1B shows a functional block diagram of information flow during capsule camera operation in the capsule camera system corresponding to FIG. 1A.

FIG. 1B is a functional block diagram of information flow during capsule camera operation. Except for optical system 114, all of these functions may be implemented on a single integrated circuit. As shown in FIG. 1B, optical system 114, which represents both illumination system 12 and optical system 14, provides an image of the lumen wall on image sensor 16. Some images will be captured but not stored in the archival memory 20, based on the motion detection circuit 18, which decides whether or not the current image is sufficiently different from the previous image. An image may be discarded if the image is deemed not sufficiently different from a previous image. Secondary sensors (e.g., pH, thermal, or pressure sensors) may be provided. The data from the secondary sensors are processed by the secondary sensor circuit 121 and provided to archival memory system 20 for storage if desired. Measurements made may be provided time stamps. Control module 22, which may comprises a microprocessor, a CPU, a digital signal processor, a digital signal processing (DSP) circuit, a state machine or random logic circuits, or any combination of these circuits, controls the operations of the modules. For example, control module 22 may use data from image sensor 16 or motion detection circuit 18 to adjust the exposure of image sensor 16.

Archival memory system 20 can be implemented by one or more nonvolatile semiconductor memory devices. There are numerous memory types that can be used; even photographic films can be used for image sensing and storage. Since the image data are digitized for digital image processing techniques, such as motion detection, memory technologies that are compatible with digital data are selected. Of course, semiconductor memories mass-produced using planar technology (which represents virtually all integrated circuits today) are the most convenient. Such memories are low-cost and may be obtained from multiple sources. Semiconductor memories are most compatible because they share common power supply with the sensors and other circuits in capsule system 110, and require little or no data conversion when interfaced with an upload device at output port 26. Archival memory system 20 preserves the data collected during the operation, after the operation while the capsule is in the body, and after the capsule has left the body, up to the time the data is uploaded. This period of time is generally less than a few days. A nonvolatile memory is preferred because data is held without power consumption, even after the capsule's battery power has been exhausted. Suitable non-volatile memory includes flash memories, write-once memories, or program-once-read-once memories. Alternatively, archival memory system 20 may be volatile and static (e.g., a static random access memory (SRAM) or its variants, such as VSRAM, PSRAM memory).

Archival memory 20 may be used to hold any initialization information (e.g., boot-up code and initial register values) to begin the operations of capsule system 110. The cost of a second non-volatile or flash memory may therefore be saved. That portion of the non-volatile can also be written over during operation to store the selected captured images. After the capsule passes from the body, it is retrieved. Capsule housing 10 is opened and input port 16 is connected to an upload device for transferring data to a computer workstation for storage and analysis.

Figure 2:
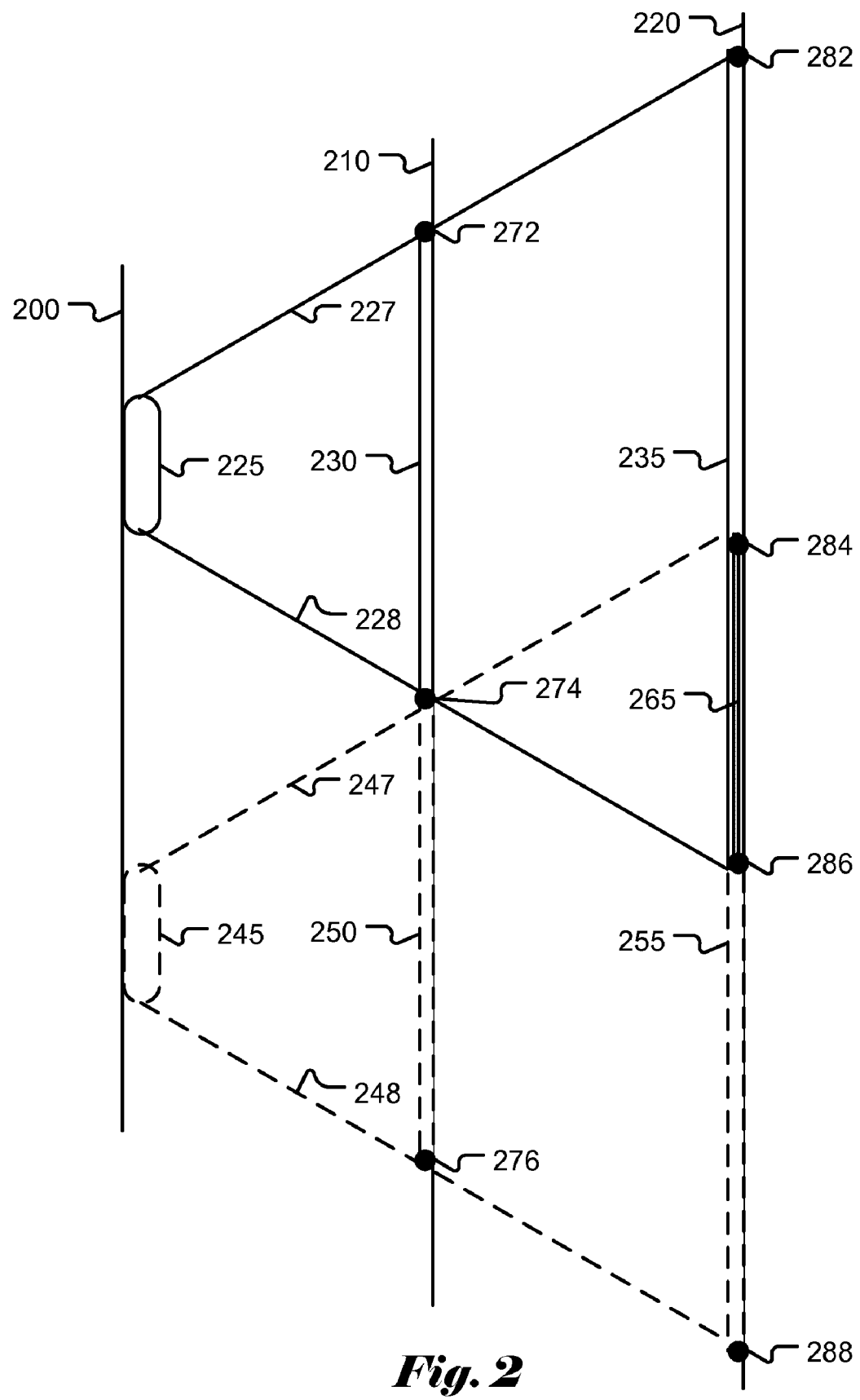
FIG. 2 shows an exemplary scenario of capsule camera field of view at two different locations inside GI track sections corresponding to two different diameters.

FIG. 2 illustrates an exemplary scenario of field of view for a capsule camera inside the GI tract. The field of view is an imaging area covered by the camera from edge to edge. While the field of view is illustrated in one dimension, it is understood by a person skilled in the art that the field of view is two dimensional. The capsule camera is at the first location 225 inside the GI tract. The lumen walls 200 and 210 indicate a section of GI tract having a smaller diameter such as small intestines. The lumen walls 200 and 220 indicate a section of GI tract having a larger diameter such as colons. Lines 227 and 228 indicate the extent of field of view at the first location. The imaging area for the lumen wall 210 is the area 230 extending from point 272 to point 274. At the same first location, the respective imaging area for a GI tract section having the larger diameter is indicated as area 235 extending from point 282 to point 286. Now, the capsule camera moves to the second location 245 inside the GI tract having a field of view indicated by edges 247 and 248. The respective imaging area for the lumen wall 210 is shown as area 250 extending from point 274 to point 276. On the other hand, the respective imaging area for the lumen wall 220 is shown as area 255 extending from point 284 to point 288. For lumen wall 210, the two imaging areas 230 and 250 are non-overlapping while for lumen wall 220, the two imaging areas 235 and 255 have a certain overlapping area. Therefore, it is reasonable that the metric of motion measured between images corresponding to areas 230 and 250 is larger than that corresponding to areas 235 and 255. The illustration in FIG. 2 qualitatively demonstrates the effect of GI tract diameter on the motion metric measurement. In actual case, the camera movement between a reference image and an underlying image is not expected to be so substantial.

The motion detector relies on the metric of motion measured and a threshold to control image capture. When the measured metric of motion is larger than a threshold, the motion detector may declare that a motion is detected and the underlying image is captured. Alternatively, the motion detector may control image capture by adjusting image compression ratio (the ratio of the original image size to the compressed image size). For example, when a larger metric of motion is measured, a higher image quality may be desired and the compression ratio can be adjusted lower accordingly.

While the above description illustrates the impact of GI tract diameter on the metric of motion measurement, it may not be easy to fully and precisely quantify the relationship between the metric of motion and the GI tract diameter. Furthermore, the information about the GI tract diameter or the distance between the camera and the lumen wall being imaged may not be readily available to the motion detector. However, there are some image processing techniques that may help to derive information associated with the distance between the capsule camera and the lumen wall being imaged. For example, a texture or feature on the lumen wall will appear to be larger when imaged at a closer distance. Consequently, the captured image at a closer distance will have lower spatial frequency than the captured image at a farther distance. Therefore, the spatial frequency of the underlying image can provide some indication about the distance. There are various techniques to calculate spatial information of an underlying image. For example, the discrete cosine transform (DCT) that is often used for image compression provides an easy way to assess the spatial characteristics of the underlying image. Subband analysis is another technique that can exploit the spatial characteristics of underlying images. Presumably an underlying image corresponding to the lumen wall imaged at a farther distance contain more high frequency information and will show more energy in higher bands of subband images. Higher spatial frequency contents may also be reflected in the gradient:

$$\nabla I(x, y) = \left(\frac{\partial I}{\partial x}, \frac{\partial I}{\partial y}\right), \tag{1}$$

where I(x,y) is the image intensity at location (x,y), $$\frac{\partial I}{\partial x}$$

is the gradient in the x direction and $$\frac{\partial I}{\partial y}$$

is the gradient in the y direction. A simplified form of gradient may be calculated by taking the differences between an image and its horizontally shifted version and the differences between the image and its vertically shifted version, i.e.:

$$\frac{\partial I}{\partial x} = \frac{I(x+1, y) - I(x, y)}{2}, \tag{2}$$

and $$\frac{\partial I}{\partial y} = \frac{I(x, y+1) - I(x, y)}{2}. \tag{3}$$

An estimate on distance based on the gradient can be simplified as the sum of the magnitudes in both x and y directions, i.e.:

$$G = \sum_{x,y} \left|\frac{I(x+1, y) - I(x, y)}{2}\right| + \left|\frac{I(x, y+1) - I(x, y)}{2}\right|, \tag{4}$$

where the summation is over the pixels of the image. However, in order to conserve power, the above summation may be taken over a partial frame instead of the full frame.

One of the above mentioned techniques or a combination of the above mentioned techniques can be used to estimate or gauge the distance between the capsule camera and the lumen wall being imaged. Beside the above mentioned methods, the LED light intensity may be used as an indication of the diameter of the GI tract section. The capsule camera system incorporates a lighting feedback control to maintain the LED lighting level. At the section with smaller GI tract diameter, the light shed on the lumen wall will be brighter. Therefore, the LED lighting control will tend to reduce the electric current supplied to the LED lights to reduce the light intensity. The LED lighting control information is available to the control module 22. Therefore, the LED lighting information can be used as an indication of the diameter of the GI tract. Based on the derived distance information, the threshold can be adjusted accordingly to properly capture images.

While the above mentioned techniques can provide useful information regarding to the distance between the capsule camera and the lumen wall being imaged, some complicated computations may be required. There are also some heuristic approaches that require minimal computations. For example, the number of skipped images may provide some indication about the capture control adjustment. When the underlying images are captured too frequent, it may be an indication that the motion detection threshold is too low. On the other hand, when the underlying images are captured too infrequent, it may be an indication that the motion detection threshold is too high. Accordingly, the motion detection threshold can be adjusted to maintain the frequency of capture in a proper range.

Figure 3:
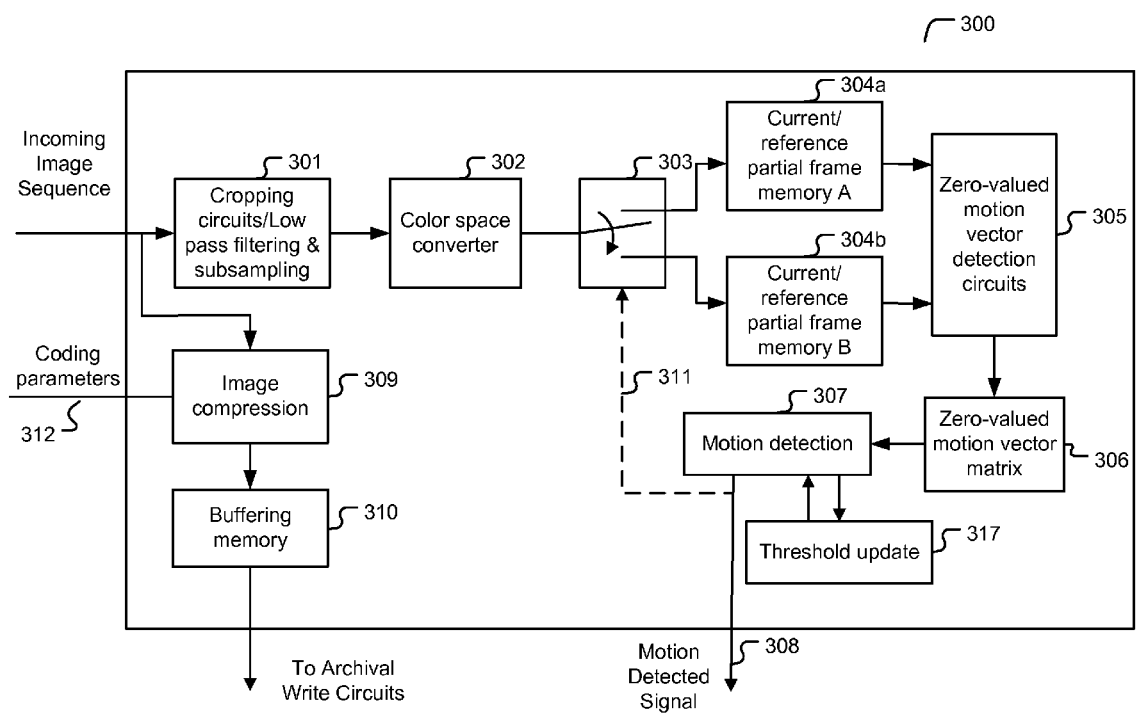
FIG. 3 is a block diagram illustrating implementation for motion detector based on zero-valued motion vectors, according to one embodiment of the present invention.

FIG. 3 is a block diagram illustrating an implementation for motion detector 18 according to one embodiment of the present invention. As shown in FIG. 3, the current digitized image from the camera sensor is received and processed in processing circuit 301, using such techniques as cropping, low-pass filtering, sub-sampling and decimation to prepare the image data for further processing at a selected resolution. A color space conversion may be performed in color space converter 302, which converts the image data from, for example, an RGB representation to a CYM representation, or a YUV representation (i.e., luma and chromas). In this manner, the image may be captured or archived using a different representation than that used for motion detection. The image is then stored in one of two partial frame buffer 304a and 304b via the switch 303. The other one of partial frame buffers 304a and 304b contains a reference image, which is the previous stored, i.e., captured, image. A pair of full resolution frame buffers may be used instead of the two partial frame buffers 304a and 304b if the technology of frame buffer is cost effective and the power consumption associated with processing the full resolution is low. Nevertheless, the use of partial frame buffers still offers great advantage of smaller storage space, lower power consumption for storing and accessing the partial frame buffers, and lower power consumption for processing images corresponding to the partial frame buffers.

Circuit 305 compares the partial current image with the partial reference image by detecting zero-valued motion vectors. The image stored in the partial frame buffers 304a and 304b is a processed version of partial image corresponding to a current incoming image or a previously stored incoming image. The partial image stored in the partial frame buffer 304a or 304b corresponding to a current incoming image may also be called a current image for short. Similarly, the partial image stored in the partial frame buffers 304a or 304b corresponding to a previously stored incoming image may also be called a reference image for short. To determine the zero-valued motion vectors, the current image and the reference image are each partitioned into M×N blocks, where M and N are integers. For each block in the current image, a measurement of differences between corresponding pixels of respective blocks is calculated. According to the outcome of this measurement of differences, each block is declared as having a zero-valued motion vector or not. The measurement of differences may be based on the sum of absolute differences (SAD), the mean squared error (MSE), or simply a count of pixels having difference larger than a threshold. The metric for this case can be the percentage of blocks not having zero-valued motion vector and is calculated in block 306. Both computations for determining zero-valued motion vector and determining the percentage of blocks having non-zero-valued motion vector are considered low-power processing due to the simplicity of the processing.

Motion detection 307 and threshold update 317 then evaluates the results to determine whether or not the current image is to be stored and then updates the threshold. In this instance, the percentage of non-zero-valued motion vector blocks (a non-zero-valued motion vector block is a block that doesn't satisfy the criterion of zero-valued motion vector) is compared against a threshold. If the percentage of non-zero-valued motion vector blocks is greater than the threshold, a motion is detected. Conversely, if the percentage of non-zero-valued motion vectors is less than the threshold, no motion is detected. The initial threshold may be pre-assigned or retrieved from a non-volatile memory in the system during the startup. During operation, the updated threshold values may be stored and read from temporal storage space such as registers in the system, where the register may be located in the control module 22, the motion detector 18, the module for implementing the threshold update, or any part of the system that is cost effective and. The result of motion detection 307 is also used to control write switch 303. If the a motion is detected, the motion detection 307 output will cause the switch 303 to change its position so that the memory holding the partial current frame becomes a partial reference frame and the memory holding the previous partial reference frame is open for the future partial current frame. If motion is not detected, the current incoming image is not to be stored and the partial frame buffer containing the current image can be overwritten by the next current image. If motion is detected, a motion detection signal 308 is asserted to cause a compressed copy of the current incoming image (stored in buffering memory 310) to be stored in archiving memory 20.

The motion detected signal may also include information associated with more capture control beside the capture/skip decision. For example, the outcome of the motion detection 307 may be used to select a compression ratio/picture quality, or the resolution or frame rate to apply to the image being stored. The motion detected signal for this case may be a rank of non-zero-valued vector blocks such as a rank from 1 to 9 corresponding to degrees of non-zero-valued vector blocks exceeding the threshold. A rank of 1 may present a highest range of percentage of blocks being identified as non-zero valued vector, such as 90% to 100% (assuming the threshold is set to 10%). A rank of 9 may represent non-zero-valued vector blocks between 10% and 20%. A rank of 1 may be associated with a lower compression ratio to preserve more picture quality. On the other hand, a rank of 9 is associated with a higher degree compression to conserve storage space. If the percentage of non-zero-valued vector blocks is less than the threshold (10% in this exemplary case), the underlying image is not captured at all, i.e., skipped. The motion detected signal 308 can be coupled to the coding parameters 312 to facilitate such capture control. Before the current incoming image is stored in archival memory 20, image compression circuit 309 compresses the current incoming image according to a selected data compression algorithm if desired. The compressed image in data buffer 310 is then transferred into archival memory 20 under control by control module 22. If the storage capacity of the on-board archival memory or the power consumption associated with transmitting an uncompressed image through the wireless transmitter is not a concern, an uncompressed image can be stored on-board or transmitted to the base station through the wireless transmitter. In this case, the image compression module 309 may be bypassed.

The threshold block 317 is responsible for threshold update and it works closely with the motion detection block 307. The motion metric received from the zero-valued motion vector matrix and the output (motion detected signal 308) of the motion detector may be used by the threshold update block 317. Furthermore, the previous values of the motion metric received and the previous values of output from the motion detectors 307 can be used for threshold update. The threshold update can be represented as a function of the current and previous values of the motion metrics, and the present and previous results of the motion detector. Several examples of threshold update corresponding to the system of FIG. 3 will be discussed later. The threshold update module 317 can be implemented in software codes running on a digital signal processor, a microcontroller, or a CPU within the hardware system. The threshold update 317 may also be implemented in hardware such as finite state machine (FSM) or digital logics. The FSM or digital logics may be implemented in the same circuit as the motion detector 307, the control module 22, or other module in the hardware system. Therefore, the implementation of the threshold update 317 is not explicitly shown in FIG. 1. However, it is understood that the threshold update 317 is embedded in other part of the hardware system.

The motion detected signal 308 is used to control image capture. If the motion detected signal 308 is asserted, the signal will cause an underlying image to be captured. As shown in FIG. 3, the motion detected signal 308 may cause an image to be compressed (block 309), stored in buffer (block 310), and transferred to on-board archival memory 20. At the same time, the motion detected signal 308 will also cause the switch 303 to be flipped as shown as the dashed line 311. The action for causing the switch 303 to flip and the action to cause the image to be written to the archival memory 20 can be achieved through control circuits which are not explicitly shown in FIG. 3. However a control circuit for causing the switch 303 to flip or the image to be written to the archival memory 20 is well known by those skilled in the art. The control circuit may also be implemented as part of the motion detector, part of the control module 22, or other part of the hardware system.

In one embodiment of the present invention, the threshold is updated automatically. A register having a plurality of data storage space is utilized to store the outcome of the motion detection as either a captured (i.e. stored) image or a skipped (i.e. non-captured) image. The register is accessible by the threshold update module 317 and is used for updating the threshold. Based on the capture information recorded in the register, the number of skipped images between the currently captured incoming image and the previously captured incoming image can be determined. The number of skipped images is denoted as $N_{skip}(t)$, where t is the index associated with captured images. The average number of skipped images is denoted as $\overline{N}_{skip}(t)$, where t is the index associated with captured images. An initial value of the average number of skipped images may be provided and the average number of skipped images can be updated every time when an image is captured according to:

$$\overline{N}_{skip}(t) = [\overline{N}_{skip}(t-1) + N_{skip}(t)]/2 \quad (5)$$

The average number of skipped images can also be updated according to other formulas. Instead of averaging the current number of skipped images and the immediate previous average number of skipped images, the average number of skipped images can be updated as a weighted sum of previous average numbers of skipped images and the current number of skipped images:

$$\overline{N}_{skip}(t) = \sum_{i=1}^{L-1} a_i \overline{N}_{skip}(t-i) + a_0 N_{skip}(t), \quad (6)$$

where $a_i$, $i=0, \ldots, L-1$, is the weighting factor and $$\sum_{i=0}^{L-1} a_i = 1.$$

Choosing weighting factor, $a_i$, is a system design issue. In the case of L=2, and $a_0=a_1=\frac{1}{2}$, the equation (6) becomes equation (5). In one embodiment of the present invention, the weighting factor is designed to let more recent average number of skipped images have more influence on the updated average number of skipped images. In other words, $a_i > a_j$ if $i<j$. For example, in the case of L=4, the weighting factors can be $\{\frac{1}{2}, \frac{1}{4}, \frac{1}{8}, \frac{1}{8}\}$ or $\{0.4, 0.3, 0.2, 0.1\}$ for i=0, 1, 2 and 3.

While equation (6) shows the updated average number of skipped images as a linear combination of current and previous average numbers of skipped images, a more general updating algorithm may be used. For example, the updating can be done according to the following algorithm:

$$\overline{N}_{skip}(t) = F[N_{skip}(t), \overline{N}_{skip}(t-1), \ldots, \overline{N}_{skip}(t-(L-1))] \quad (7)$$

where F is a multi-variable function with L variables. The multi-variable function can be a linear function such as the one as shown in equation (6) or a root-mean-squared function.

The average number of skipped images can be used as a heuristic in guiding the adjustment of the threshold. For example, the desired average number of skipped images may be within a range between a minimum average skipped images, $\overline{N}_{min}$ and a maximum average skipped images, $\overline{N}_{max}$. On the other hand, the threshold is adjusted according to the average number of skipped images. If the average number of skipped images is less than $\overline{N}_{min}$, it indicates that the images are captured too frequently. Therefore, the threshold value can be increased to lower the frequency of image capture. However, the threshold should be tested for not exceeding a maximum value, otherwise it is not updated. If the number of skipped images is larger than $\overline{N}_{max}$, it indicates that the images are captured too infrequently. Therefore, the threshold value can be decreased to increase the frequency of image capture. However, the threshold should be tested for not exceeding a minimum value, otherwise it is not updated. When a threshold is increased or decreased, the step size of change can be designed to achieve a design speed of response. A step size of too large may cause system instability. A step size too small may take quite some time to reach a desired point.

In another embodiment, the motion detection output can also be used to control the compression ratio of underlying images. Instead of making hard decision as to either capture an image or skip an image, the capture control can also be more gradual. For example, an image can be compressed less if motion is detected and compressed more if no motion is detected. Furthermore, instead of making hard decision on whether a motion is detected, the motion metric may be used directly to control image capture. For example, the compression ratio (the ratio of the original image size to the compressed image size) can be inversely proportional to the motion metric. In other words, for images having larger motion, less compression is applied so as to preserve better image quality. Blocks 309 and 310 illustrate the case that capture control is applied to vary the compression ratio. The coding parameters 312 are used to change the settings for image compression 309 and the coding parameters are related to motion metrics and can be calculated by motion detector 307. Alternatively, an incoming image can be captured and stored in on-board storage if a motion is detected. In this case, the captured image can be either compressed or non-compressed. If a compressed format is selected, a fixed compression ratio can be used.

Figure 4:
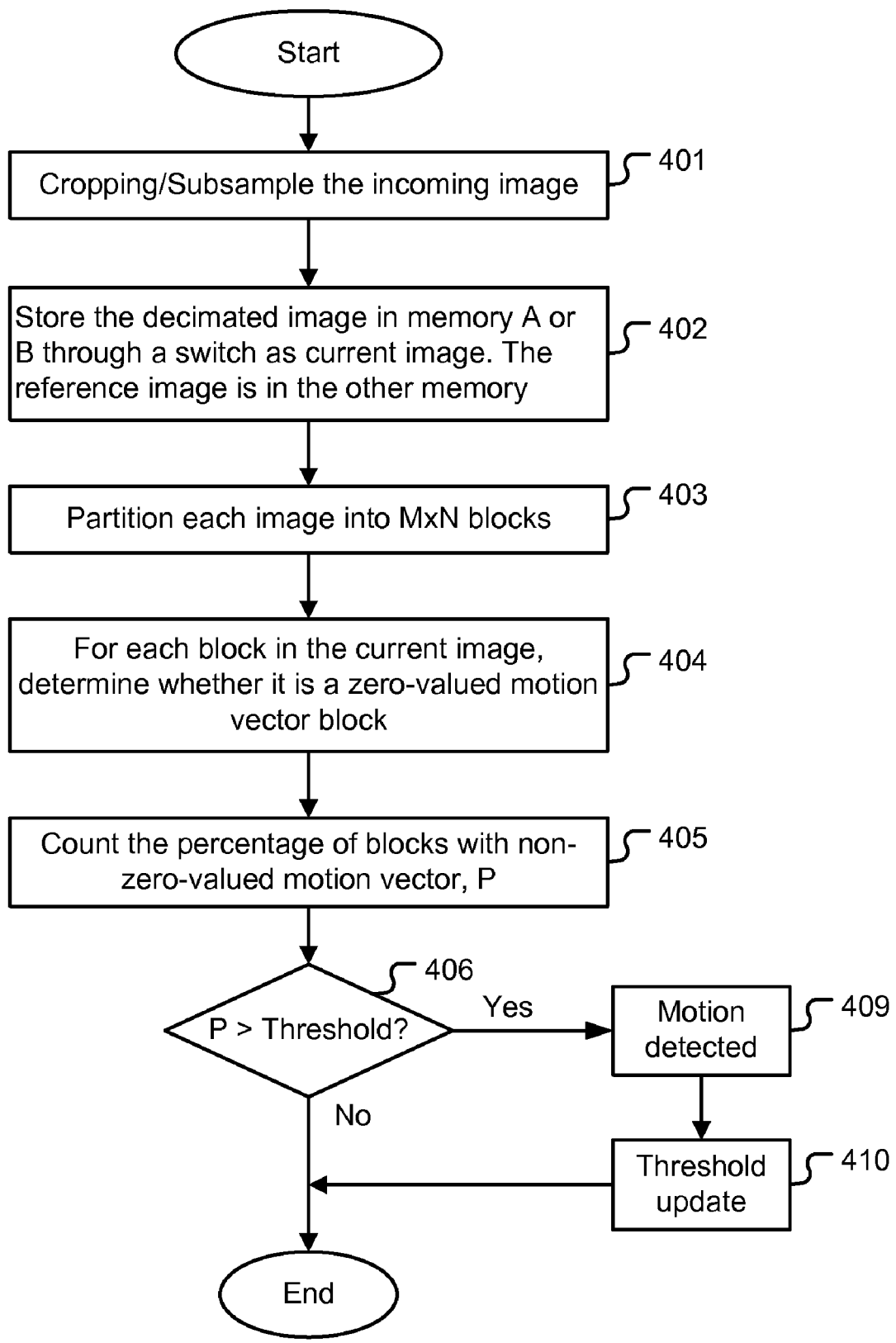
FIG. 4 is a flow chart illustrating the operations related to motion detection in implementation of FIG. 3, according to one embodiment of the present invention.

FIG. 4 is a flow chart illustrating the operations related to motion detection in implementation 300. The incoming image may be cropped and subsampled as shown in block 401. After the processing, the decimated image is stored either in memory A or memory B depending on which memory is designated as the current frame as shown in block 402. The image is then partitioned into M×N blocks as shown in block 403. In block 404, each block is processed to determine whether it is a zero-valued motion vector block, and in block 405 the percentage of non-zero-valued motion vector blocks is calculated as the metric of motion. The metric is then compared against a threshold in block 406. If the metric is greater than a threshold, it is declared that a motion is detected 409. The threshold is then updated in block 410. One embodiment for the threshold update is according to a heuristic related to the number of skipped images as described above or according to distance estimate between the capsule camera and the lumen wall being imaged if it is available.

Figure 5:
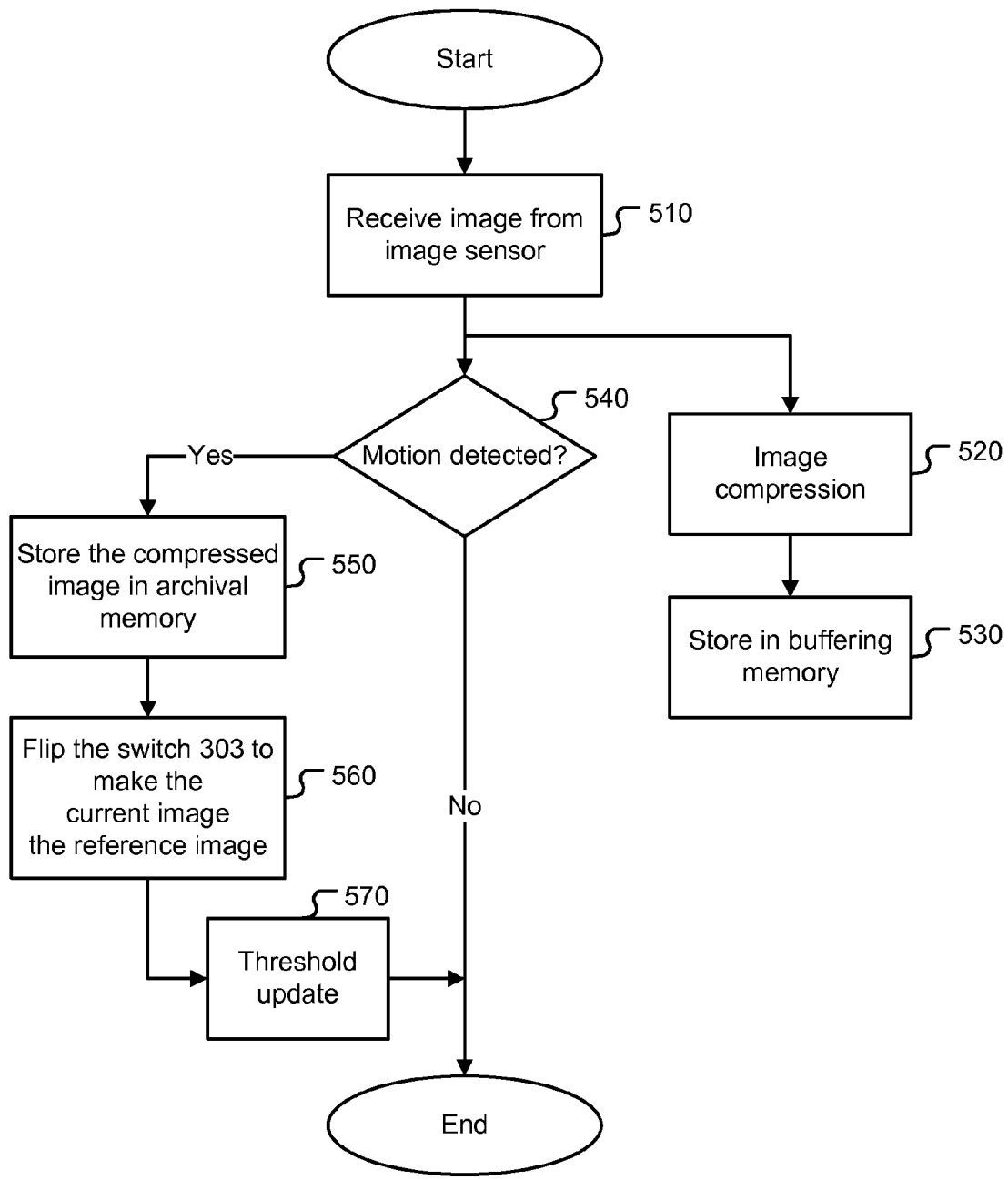
FIG. 5 is a flow chart illustrating the operations relating to data storage in implementation of FIG. 3, according to one embodiment of the present invention.

FIG. 5 is a flow chart illustrating the operations relating to data storage in implementation 300 according to one embodiment of the present invention. The image is received from image sensor in block 510. One route shows that the image in compressed and stored in a buffer for possible on-board storage as shown in blocks 520 and 530. On the other hand, the motion detection decision 540 may cause the image stored in buffer 530 to be transferred into archival memory 20 (the action of block 550) when motion is detected (the yes path from block 540). Upon the detection of motion, besides causing the block 550 to store the compressed image in archival memory, it also causes the switch 303 to flip and to make the current image the reference image as shown in block 560. The threshold is then updated accordingly as shown in block 570.

Note that, in the above embodiments, only zero-valued motion vector is determined in order to conserve processing power. Nevertheless, regular motion estimation can also be used that searches for possible motion vectors within a range. When a regular motion estimation is used, the motion vectors in the forward direction along the length of the GI tract (i.e., +y direction) are of interest. Movement in the −y direction represents a retrograde motion. Presumably, the optical view after the retrograde motion has already been captured previously. Alternatively, we can reduce the weight given to the x-component of the motion vector, so that some motion vectors with some x-component motion can be rounded to [0, 0]. When a regular motion estimation is used, the metric of motion can be measured as the dominant motion vector (i.e., a motion vector that has the highest occurrence in the image), the average motion vector or median motion vector. The metric of motion can be used to determine whether an underlying image should be captured or a proper compression ratio for the underlying image.

Figure 6:
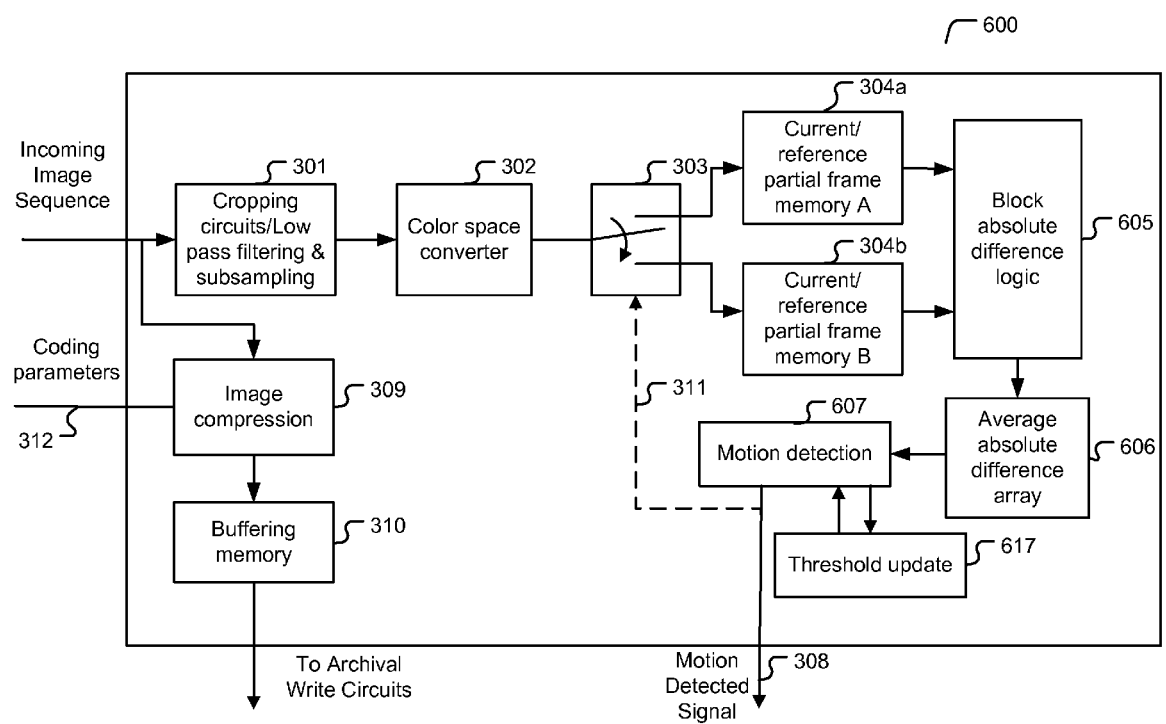
FIG. 6 a block diagram illustrating implementation for motion detector based on the variance of differences, according to one embodiment of the present invention.
Figure 7:
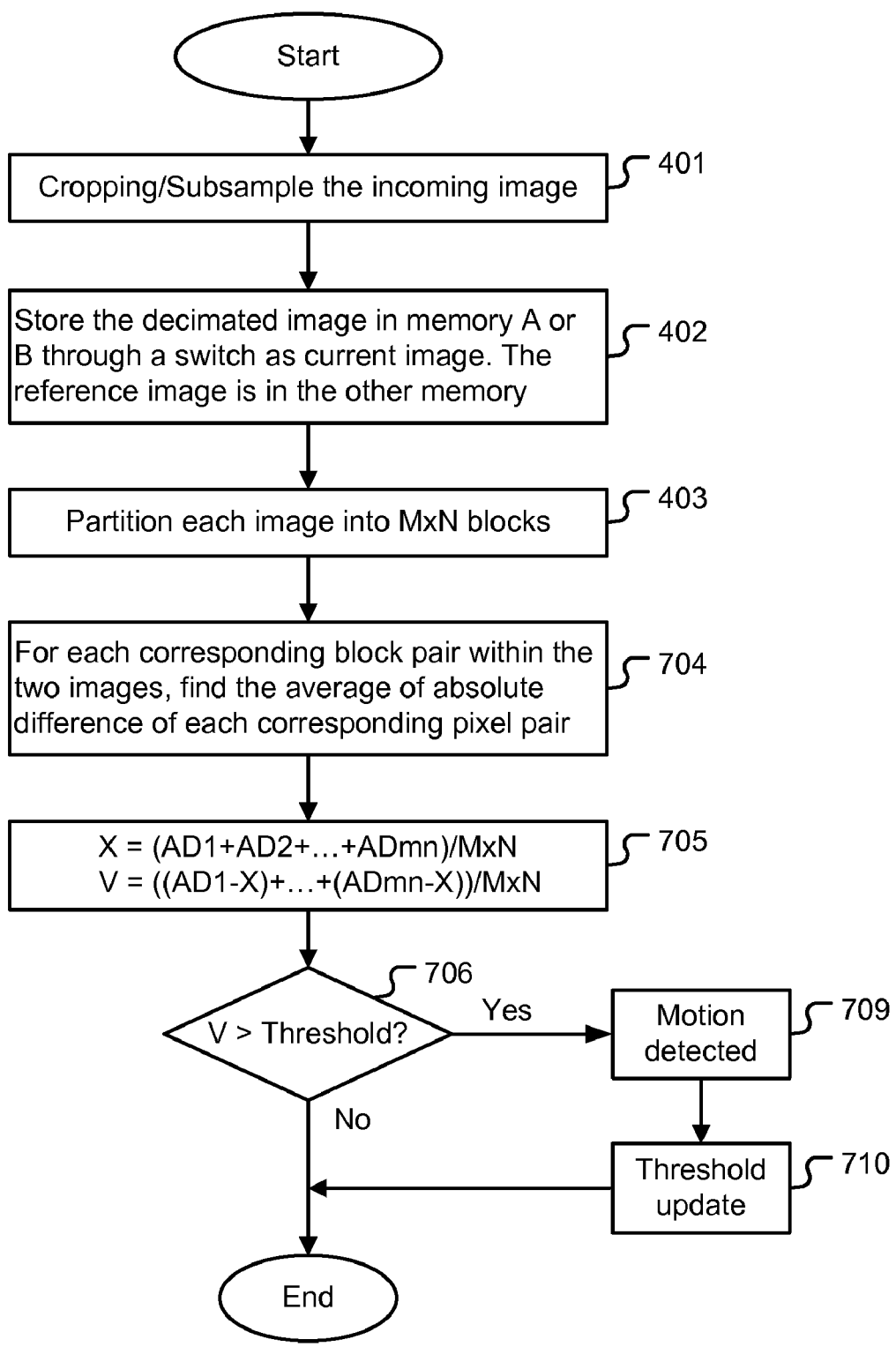
FIG. 7 is a flow chart illustrating the operations related to motion detection in implementation of FIG. 6, according to one embodiment of the present invention.

Instead of using motion vectors, metric of motion can also be measured using differences between the current image and the reference image. The difference can be in term of absolute value or mean squared value. FIG. 6 shows an implementation 600 for image based motion detection 18 using the absolute difference approach. Implementation 600 operates substantially the same way as implementation 300 of FIG. 3, except that zero-valued motion vector detection circuits 305, zero-valued motion vector matrix 306, motion detection calculation circuit 307 and threshold update module 317 of FIG. 3 are replaced by block absolute difference logic 605, average absolute difference array 606, motion detection circuit calculation 607 and threshold update module 617. FIG. 7 is a flow chart illustrating the operations related to motion detection in implementation 600. FIG. 7 shares a number of operations with FIG. 4 discussed above. To simplify the following discussion, operations in FIG. 7 that are substantially the same as corresponding steps in FIG. 4 are assigned the same reference numeral. The storage operations for implementation 600 are substantially the same as the corresponding operations in implementation 300. Those operations are referenced to FIG. 5

As shown in FIGS. 5-7, the current digitized image is received (step 510, FIG. 5) and processed in processing circuit (block 310, FIG. 6), using such techniques as cropping, low-pass filtering, sub-sampling and decimation to prepare the image data for further processing at a selected resolution (step 401, FIG. 7). One portion of the processed image is selected for motion detection. As mentioned above, this portion may be represented at a higher resolution than the rest of the image. As in implementation 300, a color space conversion may be performed in color space converter 302. The image is then stored in one of two partial frame buffer 304a and 304b (step 402, FIG. 7). The other one of partial frame buffers 304a and 304b contains a reference image, which corresponds to a previous stored image.

Circuit 605 compares the current image with the reference image by evaluating absolute differences between the two images. To identify the differences, at step 403 (FIG. 7), the current image and the reference image are each partitioned into M×N blocks, where M and N are integers. In each corresponding block pair (i.e., a block in the current image and the block in the corresponding position in the reference image), an absolute difference between each pixel (e.g., in luminance) in the current image and the corresponding pixel in the reference image is found in block absolute difference logic circuit 605 (step 704, FIG. 7). An average for the absolute difference, denoted by $AD_i$, i=1, ..., M×N, for the block is found and provided in average absolute difference array 606. Motion detection calculation circuit 607 then evaluates the results to determine if the current incoming image is to be stored. In this instance, at step 705 (FIG. 7), a mean absolute difference, $$\bar{x} = \frac{1}{M \times N} \sum_{i=1}^{M \times N} AD_i \tag{8}$$

over the portion of image is calculated. Then, the total variance, v is calculated as:

$$v = \frac{1}{M \times N} \sum_{i=1}^{M \times N} (AD_i - \bar{x})^2. \quad (9)$$

The above variance computation involves an operation of multiplication which may be challenging for low-power implementation. Alternatively, absolute value may be used in the above variance calculation, i.e., $$v = \frac{1}{M \times N} \sum_{i=1}^{M \times N} |AD_i - \bar{x}|. \quad (10)$$

If the total variance exceeds a threshold (step 706, FIG. 7), motion is deemed detected as shown in step 709. The threshold is then updated in block 710. Conversely, if the total variance v is less than the threshold, no motion is deemed detected. If motion is detected, a motion detection signal 308 is asserted to cause the current incoming image to be stored in archiving memory 20 (step 550, FIG. 5). The partial frame buffer 304a or 304b that contains the current image is marked to become the new reference image, while the other partial frame buffer (i.e., the partial frame buffer containing the current reference image) is made available to be overwritten by the next current image (step 560, FIG. 5). If the current incoming image is not to be stored, the partial frame buffer containing the current image can be overwritten by the next current image. Before the current incoming image is stored in archival memory 20, image compression circuit 309 compresses the current incoming image according to a selected data compression algorithm (step 520, FIG. 5). The compressed image in data buffer 310 is then transferred into archival memory 20 (step 530, FIG. 5) under the control by a control circuit which is not explicitly shown. However the control circuit can be implemented by the control module 22, the image based motion detection 18, or other part of the hardware system.

The threshold update 617 for the embodiment of the present invention as shown in FIG. 6 is similar to that shown in FIG. 3. The adjustment can be based on the heuristic of frequency of skipped images. For example, the desired average number of skipped images may be within a range between a minimum average skipped images, $\bar{N}_{min}$ and a maximum average skipped images, $\bar{N}_{max}$. The threshold is adjusted according to the average number of skipped images. If the number of skipped images is less than $\bar{N}_{min}$ it indicates that the images are captured too frequently. Therefore, the threshold value can be increased to lower the frequency of image capture. However, the threshold is tested for not exceeding a maximum value, otherwise it is not updated. If the number of skipped images is larger than $\bar{N}_{max}$, it indicates that the images are captured too infrequently. Therefore, the threshold value can be decreased to increase the frequency of image capture. However, the threshold is tested for not exceeding a minimum value, otherwise it is not updated. When a threshold is increased or decreased, the step size of change can be designed to achieve a design speed of reaction. A step size of too large may cause system instability. A step size too small may take quite some time to reach a desired point. Again, the threshold update module 617 can be implemented in software codes running on a digital signal processor, a microcontroller, or a CPU within the hardware system. The threshold update 617 may also be implemented in hardware such as finite state machine (FSM) or digital logics. The FSM or digital logics may be implemented in the same circuit as the motion detector 607, the control module 22, or other module in the hardware system.

Alternatively, the variance can be used as a soft control for image capture. Instead of capturing an underlying image or skipping an underlying image depending whether the variance is exceeding a threshold or not, the variance can be used to control the compression ratio of an underlying incoming image. When a larger variance value is measured, the underlying incoming image may be undergoing a larger motion and the image should be captured with higher quality, i.e. a smaller compression ratio. Conversely, when a smaller variance is measured, the underlying image may have little motion and a larger compression ratio can be selected.

Figure 8:
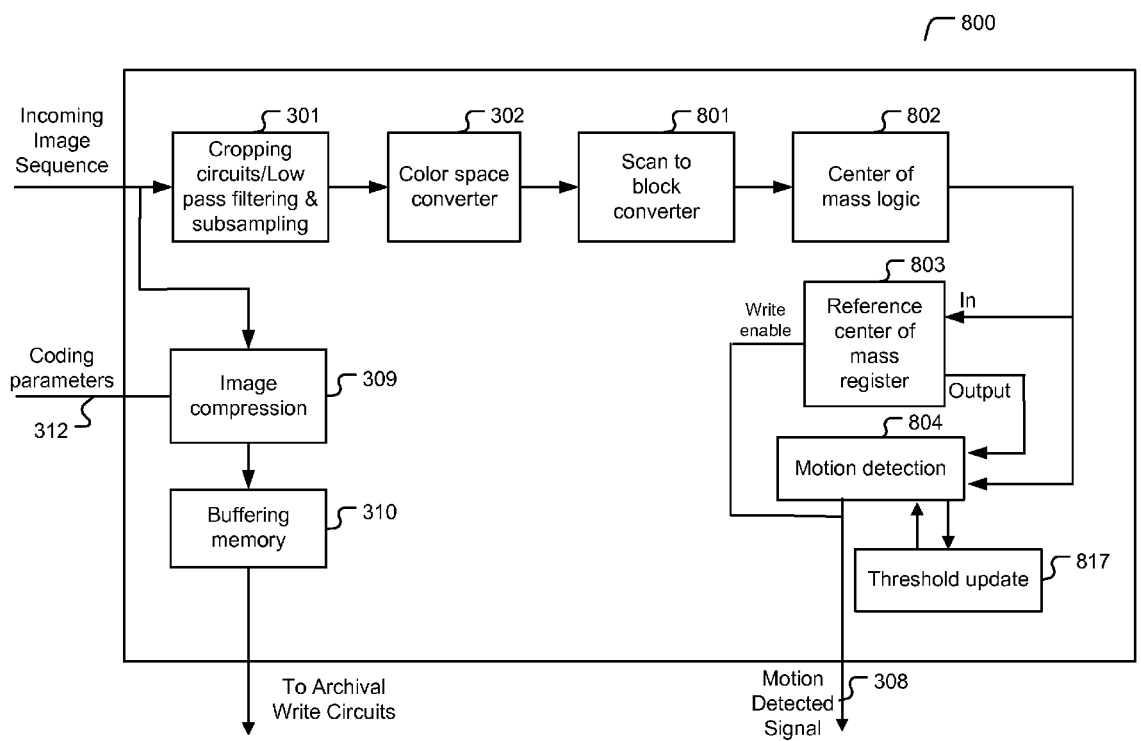
FIG. 8 is a block diagram illustrating implementation for motion detector based on difference of centers of mass, according to one embodiment of the present invention.
Figure 9:
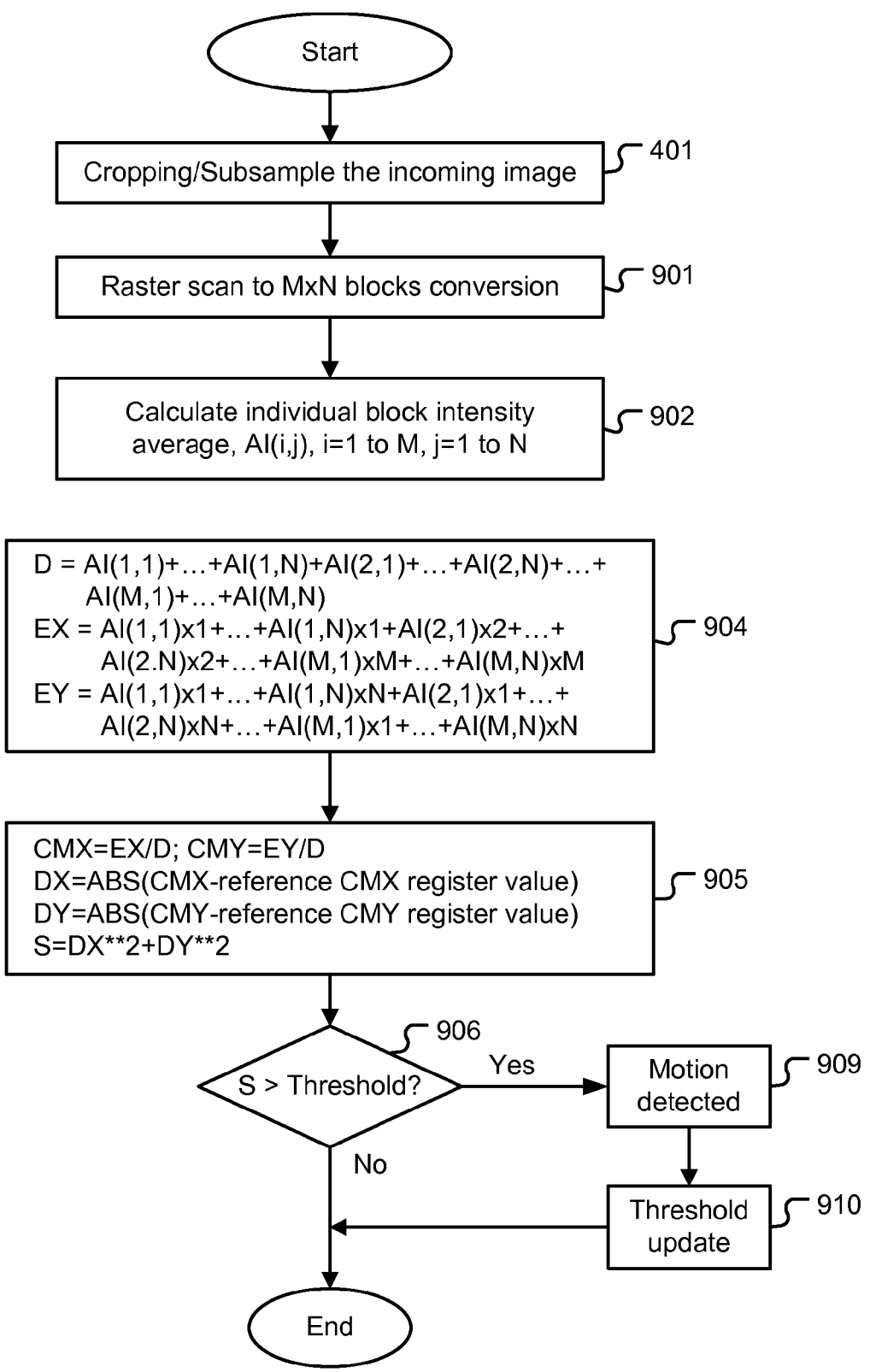
FIG. 9 is a flow chart illustrating the operations related to motion detection in implementation of FIG. 8, according to one embodiment of the present invention.
Figure 10:
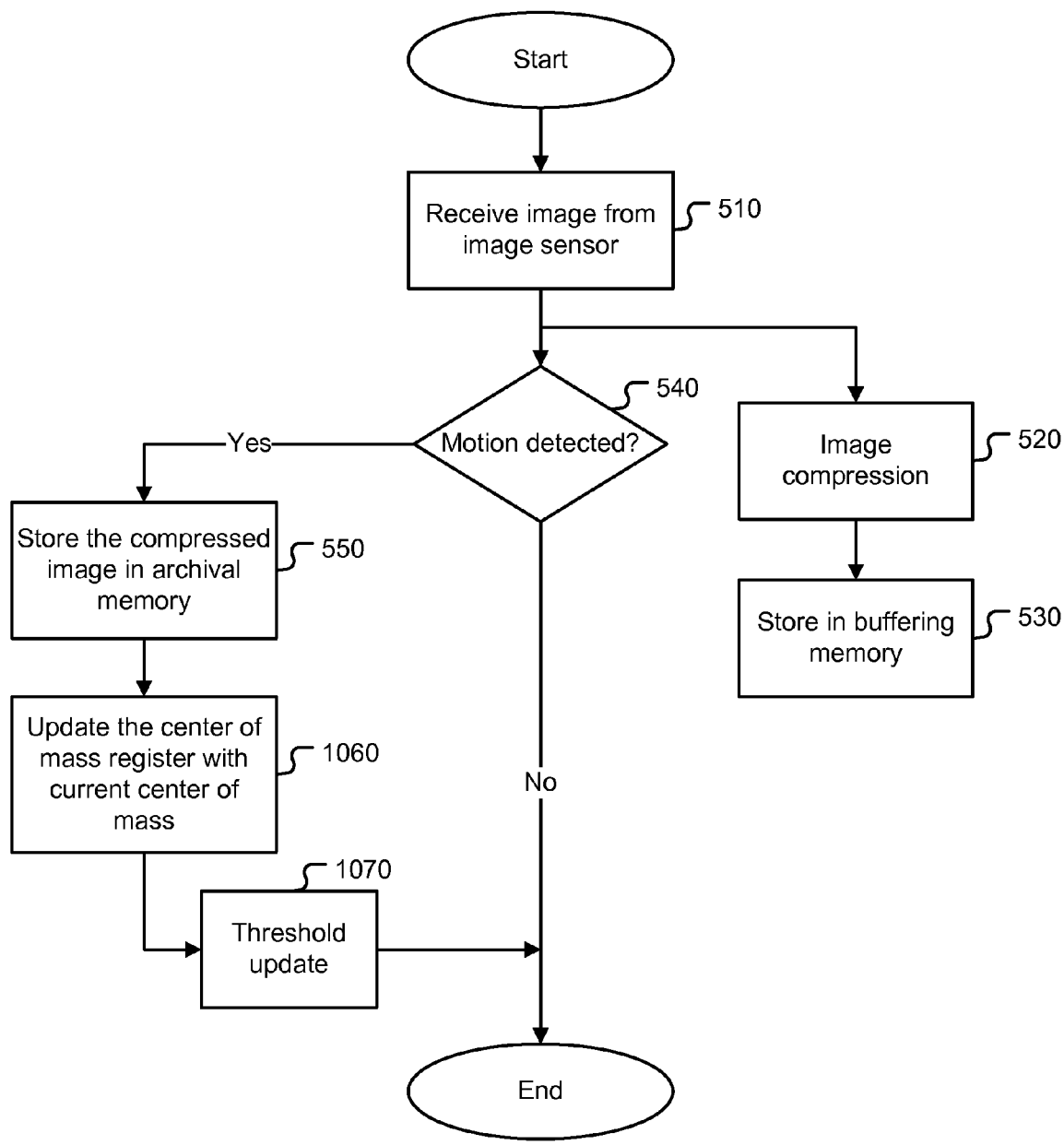
FIG. 10 is a flow chart illustrating the operations related to data storage in implementation of FIG. 8, according to one embodiment of the present invention.

Instead of using motion vectors or absolute difference, motion detection can also be performed according to yet another embodiment of the present invention, using a "center-of-mass" approach. FIG. 8 shows an implementation 800 using the center-of-mass approach. Implementation 800 includes operations that are substantially the same way as corresponding operations in implementation 300 of FIG. 3. These corresponding operations between FIGS. 3 and 8 are assigned the same reference numerals. FIGS. 9-10 are, respectively, flow charts illustrating the operations related to motion detection and data storage in implementation 800. FIGS. 9-10 share a number of operations with FIGS. 4-5 discussed above. To simplify the following discussion, operations in FIGS. 9-10 that are substantially the same as corresponding operations in FIGS. 4-5 are assigned the same reference numeral.

As shown in FIGS. 8-10, the current digitized image is received (step 510, FIG. 10) and processed in processing circuit 301, using such techniques as cropping, low-pass filtering, sub-sampling and decimation to prepare the image data for further processing at a selected resolution (step 401, FIG. 9). As in implementation 300, a color space conversion may be performed in color space converter 302. In implementation, the luminance value in each pixel of the current image is stored in M×N blocks in raster scan-to-block converter 801 (step 901, FIG. 9). Center-of-mass logic circuit 802 then calculates the center-of-mass for the image. To calculate the center-of-mass, the average intensity $AI_{ij}$, i=1, ..., M and j=1, ..., N, of each block is first calculated (step 904, FIG. 9). A total D of the average intensities over all the blocks, i.e., $$D = \sum_{i,j} AI_{ij}$$

is calculated. Then the moments $E_x$ and $E_y$ along the orthogonal directions are calculated. The moments are given by $$E_x = \sum_{i,j} i * AI_{ij} \quad (11)$$

and $$E_y = \sum_{i,j} j * AI_{ij}.$$

The center-of-mass CM ($CM_x$, $CM_y$) for the image is then provided by:

$$CM_x = \frac{E_x}{D} \quad (12)$$

and $$CM_y = \frac{E_y}{D}.$$

The reference center-of-mass $CM_{ref}(CM_{ref\_x}, CM_{ref\_y})$ value, corresponding to the center-of-mass of the previous stored image, is stored in reference register 803. Motion detection calculation circuit 804 then evaluates the results to determine whether or not the current image is to be stored. In this instance, at step 905 (FIG. 9), the values $D_x$ and $D_y$ of the differences between the center-of-mass of the current image and the center-of-mass of the reference image along the orthogonal directions are then calculated. These differences are given by:

$$D_x = CM_x - CM_{ref\_x} \text{ and } D_y = CM_y - CM_{ref\_y} \quad (13)$$

The metric $S = D_x^2 + D_y^2$ then provides a measure for the motion in the current image. If metric S exceeds a threshold (step 906, FIG. 9 or 540, FIG. 10), motion is deemed detected as shown in step 909. The threshold is then updated in block 910. Conversely, if the metric S is less than the threshold, no motion is deemed detected. In some embodiments, only motion in the forward direction along the GI tract (i.e., +y direction) is of interest. Movement in the -y direction represents a retrograde motion. In that situation, the metric S may simply be $D_y$ or $D_y^2$. Alternatively, a greater weight may be given to a shift in center-of-mass in the y direction, $S = D_x^2 + wD_y^2$, w>1.

The threshold update 817 for the embodiment of the present invention as shown in FIG. 8 is similar to that shown in FIG. 3. The adjustment can be based on the heuristic of frequency of skipped images. For example, the desired average number of skipped images may be within a range between a minimum average skipped images, $\overline{N}_{min}$ and a maximum average skipped images, $\overline{N}_{max}$. Again, the threshold update module 817 can be implemented in software codes running on a digital signal processor, a microcontroller, or a CPU within the hardware system. The threshold update 817 may also be implemented in hardware such as finite state machine (FSM) or digital logics. The FSM or digital logics may be implemented in the same circuit as the motion detector 804, the control module 22, or other module in the hardware system.

The motion is determined in step 540 of FIG. 10. If motion is detected, a motion detection signal 308 is asserted to cause a compressed copy of the current incoming image (in buffering memory 310) to be stored in archiving memory 20 (step 550, FIG. 10). The current center-of-mass value is stored into reference register 803 (step 1060, FIG. 10). Also, the threshold is update in step 1070. Before the current incoming image is stored in archival memory 20, image compression circuit 309 compresses the current incoming image according to a selected data compression algorithm (step 520, FIG. 10). The compressed image in data buffer 310 is then transferred into archival memory 20 under control by a control circuit not explicitly shown. However, the control circuit can be implemented in the control module 22, the motion detector 18, or other part of the hardware system.

When the center of mass is used as the metric of motion, the same threshold update technique as mentioned before can be used. The adjustment can be based on the heuristic of frequency of skipped images. For example, the desired average number of skipped images may be within a range between a minimum average skipped images, $\overline{N}_{min}$ and a maximum average skipped images, $\overline{N}_{max}$.

Alternatively, the difference of centers of mass can be used as a soft control for image capture. Instead of capturing an underlying image or skipping an underlying image depending whether the difference of centers of mass is exceeding a threshold, the difference of centers of mass can be used to control the compression ratio of an underlying image. When a larger difference of centers of mass is measured, the underlying image may be undergoing a larger motion and the image should be captured with higher quality, i.e. a smaller compression ratio. Conversely, when a smaller difference of centers of mass is measured, the underlying image may have little motion and a larger compression ratio can be selected.

Figure 11:
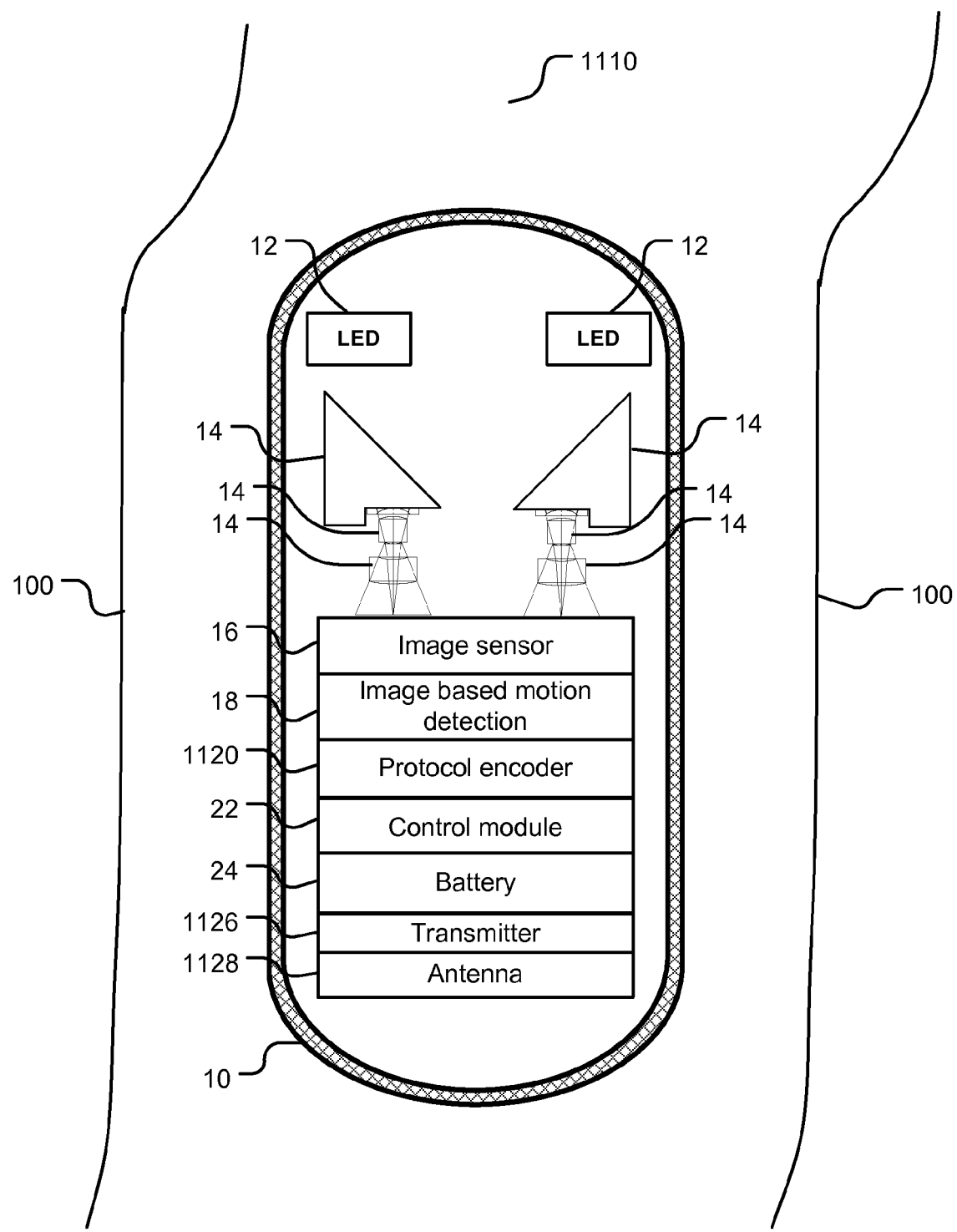
FIG. 11 shows schematically capsule camera system having a wireless transmitter, according to one embodiment of the present invention, where the capsule camera shown is inside the GI tract.

The present invention is also used for capsule camera system having a wireless transmitter to send the captured images to an external receiver instead of storing the images on board. FIG. 11 shows swallowable capsule system 110, in accordance with one embodiment of the present invention. Capsule system 110 may be constructed substantially the same as capsule system 110 of FIG. 1, except that archival memory system 20 and output port 26 are no longer required. Capsule system 1110 also includes communication protocol encoder 1120, transmitter 1126 and antenna 1128 that are used in the wireless transmission. The elements of capsule 110 and capsule 110 that are substantially the same are therefore provided the same reference numerals. Their constructions and functions are therefore not described here again. Communication protocol encoder 1120 may be implemented in software that runs on a DSP or a CPU, in hardware, or a combination of software and hardware. Transmitter 1126 and antenna system 1128 are used for transmitting the captured digital image.

Figure 12:
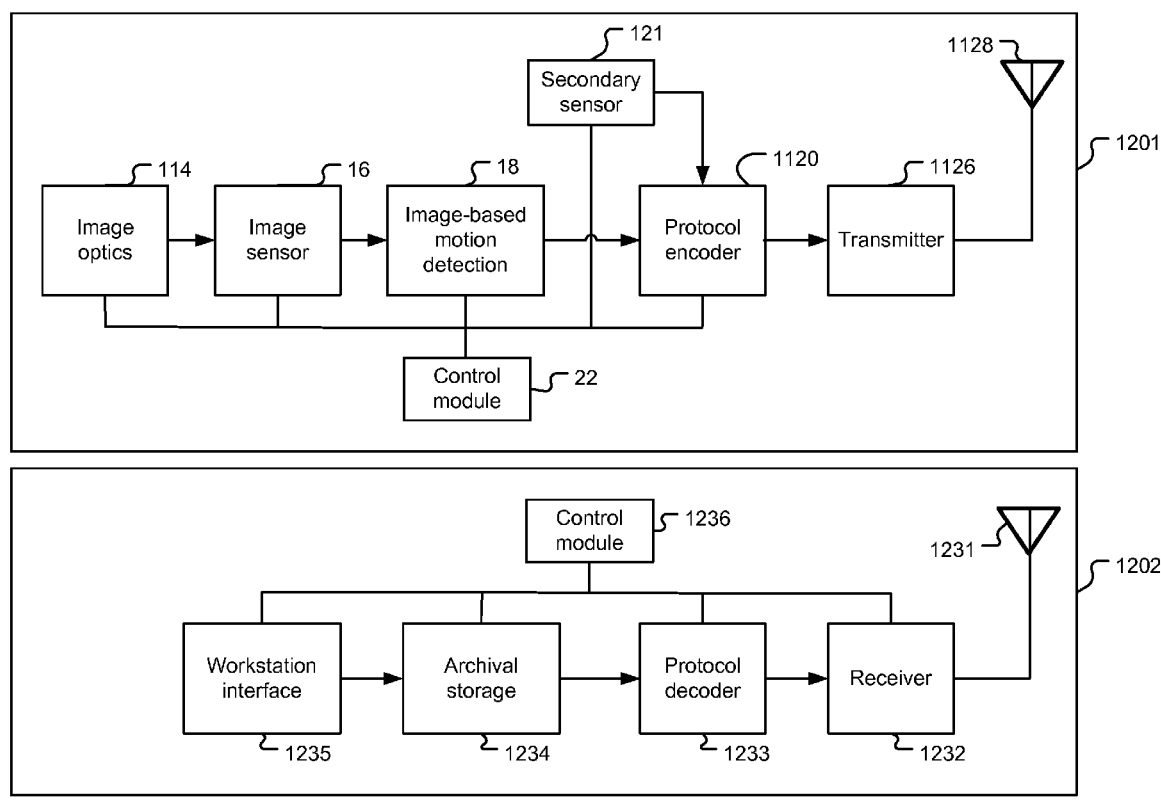
FIG. 12 is a functional block diagram of information flow in implementation during capsule camera operation in a capsule camera system having a wireless transmitter and an external base-station.

FIG. 12 is a functional block diagram of information flow of implementation of capsule system 110, during capsule camera operation. Functions shown in blocks 1201 and 1202 are respectively the functions performed in the capsule and at an external base station with a wireless receiver 1232. With the exception of optical system 114, the functions in block 1201 may be implemented on a single integrated circuit. Optical system 114, which represents both illumination system 12 and optical system 14, provides an image of the lumen wall on image sensor 16. Some images will be monitored but not transmitted from capsule system 1110, based on the motion detection circuit 18, which decides whether or not the current image is sufficiently different from the previous image. All the modules and methods for motion detection discussed above in conjunction with FIGS. 3-10 are also applicable in capsule system 110. An incoming image may be discarded if the image is deemed not sufficiently different from the previous image. An incoming image selected for transmission is processed by protocol encoder 1120 for transmission. Secondary sensors (e.g., pH, thermal, or pressure sensors) may be provided. The data from the secondary sensors are processed by the secondary sensor circuit 121 and provided to protocol encoder 1120. Measurements made may be provided time stamps. Images and measurements processed by protocol encoder 1120 are transmitted through transmitter 1126 and antenna 1128. Control module 22, which may consist of a microprocessor, a state machine or random logic circuits, or any combination of these circuits, controls the operations of the modules in capsule system 1110. As mentioned above, the benefits of selecting captured images based on whether the capsule has moved over a meaningful distance or orientation is also applicable to select captured images for wireless transmission. In this manner, an incoming image that does not provide additional information than the previously transmitted one is not transmitted. Precious battery power that would otherwise be required to transmit the image is therefore saved.

As shown in FIG. 12, a base station represented by block 1202 outside the body receives the wireless transmission using antenna 1231 of receiver 1232. Protocol decoder 1233 decodes the transmitted data to recover the captured images. The recovered captured images may be stored in archival storage 1234 and provided later to a workstation through workstation interface 1235 where a practitioner (e.g., a physician or a trained technician) can analyze the images. Control module 1236, which may be implemented the same way as control module 22, controls the functions of the base station. Capsule system 110 may use compression to save transmission power. If compression is used in the transmitted images in motion detector 18, a decompression engine may be provided in base station 1202, or the images may be decompressed in the workstation when they are viewed or processed. A color space converter may be provided in the base station, so that the transmitted images may be represented in a different space used in motion detection than the color space used for image data storage.

Figure 13:
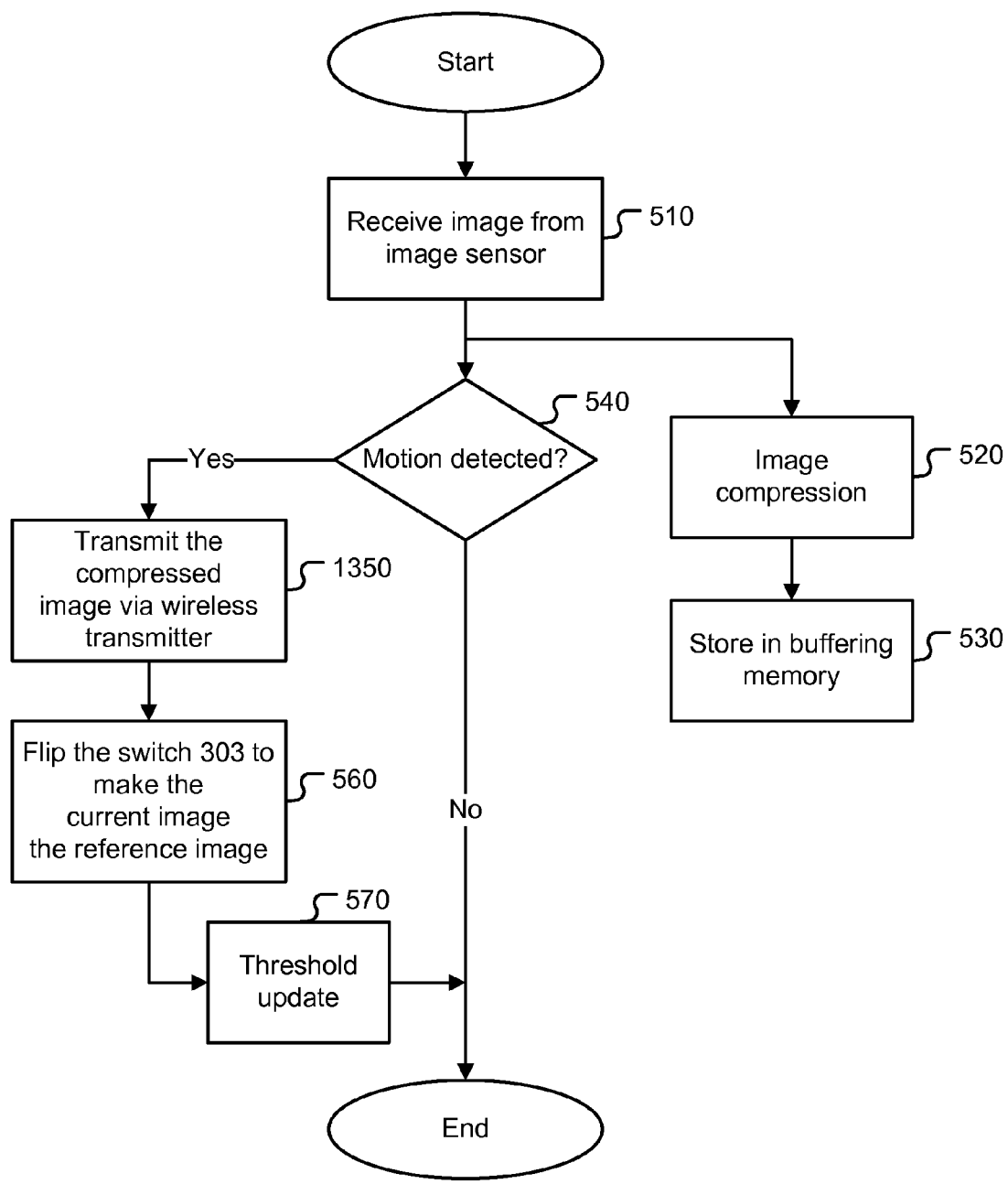
FIG. 13 is a flow chart illustrating the operations relating to image capture via wireless transmission according to one embodiment of the present invention.

The main difference between the capsule camera system in FIG. 1 and the capsule camera system in FIG. 11 is that the capsule camera system 110 of FIG. 1 uses on-board storage while the capsule camera system 1110 of FIG. 11 uses wireless to transmit the images to an external base station for off-board storage. All the modules and methods for motion detection discussed above in conjunction with FIGS. 3-10 are also applicable in capsule system 110 with minor modification. The same modules and methods for motion detection and threshold update in conjunction with FIGS. 3-10 are applicable to the capsule camera system in FIG. 11 except that whenever an image was determined to be written into the on-board archival memory is now transmitted through the wireless transmitter to the external base station. For example, the flow chart shown in FIG. 5 for the capsule camera system with an on-board storage can be modified for the capsule camera system having a wireless transmitter. The modified flow chart is shown in FIG. 13 which is substantially the same as FIG. 5 except that the step 550 for storing the captured image becomes step 1350 for transmitting the captured image via wireless transmission.

The above detailed description illustrates the specific embodiments of the present invention and is not intended to be limiting. Numerous modifications and variations within the scope of the invention are possible. The present invention is set forth in the following claims.

The invention claimed is:

1. A capsule camera apparatus, comprising:
   a housing adapted to be swallowed;
   a light source within the housing;
   an archival storage device;
   a camera within the housing for capturing a first digital image and a second digital image of a scene illuminated by the light source;
   a motion detector within the housing comprising:
      a metric measurement module coupled to the first digital image and the second digital image measures a metric of a motion between the first digital image and the second digital image;
      a motion detection module coupled to the metric measurement module detects the motion based on the metric and a threshold; and
      a threshold update module coupled to the metric measurement module and the motion detection module updates the threshold; and
   a control circuit within the housing that designates the second digital image for further processing based on the motion detected by the motion detection module.

2. A capsule camera apparatus as in claim 1, wherein a portion of the first digital image is stored in a first partial frame buffer and a portion of the second digital image is stored in a second partial frame buffer.

3. A capsule camera apparatus as in claim 2, wherein the control circuit determines which of the first and second partial frame buffers is to be overwritten by a third digital image according to the motion detected.

4. A capsule camera apparatus as in claim 1, further comprising a register for storing the metric, the register being accessible by the motion detector and/or the threshold update module during operation.

5. A capsule camera apparatus as in claim 1, wherein the metric measurement module evaluates zero-valued motion vectors between a portion of the first digital image and a portion of the second digital image.

6. A capsule camera apparatus as in claim 5, wherein the metric includes a value related to a count of zero-valued motion vectors.

7. A capsule camera apparatus as in claim 1, wherein the metric measurement module computes average absolute differences between corresponding portions of the first digital image and the second digital image.

8. A capsule camera apparatus as in claim 7, wherein the metric includes a variance of the average absolute differences.

9. A capsule camera apparatus as in claim 1, wherein the metric measurement module computes for a portion of the first digital image and a portion of the second digital image each a center-of-mass.

10. A capsule camera apparatus as in claim 9, wherein the metric depends on a difference between the centers-of-mass computed.

11. A capsule camera apparatus as in claim 1, wherein the control circuit causes a new second digital image to be captured according to the metric and the threshold.

12. A capsule camera apparatus as in claim 11, further comprising a register for storing a result of the control circuit as being captured or skipped, wherein the register being accessible by the motion detector and/or the threshold update module.

13. A capsule camera apparatus as in claim 12, wherein a number of images skipped between two captured images is counted, an initial value of an average number of skipped images is provided, and the average number of skipped images is updated according to function of a plurality of previous values of the average number of skipped images and a current value of the number of skipped images.

14. A capsule camera apparatus as in claim 13, wherein the function is a linear function having weighting factors.

15. A capsule camera apparatus as in claim 14, wherein the weighting factors have more weight on more recent previous values of the average number of skipped images.

16. A capsule camera apparatus as in claim 13, wherein the threshold is increased if the average number of skipped images is smaller than a low limit and the threshold is smaller than a maximum threshold.

17. A capsule camera apparatus as in claim 13, wherein the threshold is decreased if the average number of skipped images is larger than a high limit and the threshold is larger than a minimum threshold.

18. A method for capsule camera, comprising:
providing a housing adapted to be swallowed;
providing a light source and a camera within the housing;
providing an archival storage device;
capturing a first digital image and a second digital image of a scene illuminated by the light source;
measuring a metric of motion between the first digital image and the second digital image;
detecting a motion based on the metric and a threshold;
updating the threshold; and
designating the second digital image for further processing based on the motion detected,
wherein the measuring, detecting, updating and designating steps are performed by circuitry within the housing.

19. A method as in claim 18, wherein a portion of the first digital image is stored in a first partial frame buffer and a portion of the second digital image is stored in a second partial frame buffer.

20. A method as in claim 18, wherein said measuring the metric includes zero-valued motion vectors between a portion of the first digital image and a portion of the second digital image.

21. A method as in claim 20, wherein the metric has a value related to a count of zero-valued motion vectors.

22. A method as in claim 18, wherein said measuring the metric includes computing average absolute differences between corresponding portions of the first digital image and the second digital image.

23. A method as in claim 22, wherein the metric is related to a variance of the average absolute differences.

24. A method as in claim 18, wherein said measuring the metric includes computing for a portion of the first digital image and a portion of the second digital image each a center-of-mass.

25. A method as in claim 24, wherein the metric is related to a difference between the centers-of-mass computed.

26. A method as in claim 18, wherein the further processing includes causing a new second digital image to be captured.

27. A method as in claim 26, further comprising a register for storing a result of the further processing as being captured or skipped, wherein the register being accessible by said detecting the motion.

28. A method as in claim 27, wherein a number of images skipped between two captured images is counted, an initial value of an average number of skipped images is provided, and the average number of skipped images is updated according to a function of a plurality of previous values of the average number of skipped images and a current value of the number of skipped images.

29. A method as in claim 28, wherein the function is a linear function having weighting factors.

30. A method as in claim 29, wherein the weighting factors have more weight on more recent previous values of the average number of skipped images.

31. A method as in claim 28, wherein the threshold is increased if the average number of skipped images is smaller than a low limit and the threshold is smaller than a maximum threshold.

32. A method as in claim 28, wherein the threshold is decreased if the average number of skipped images is larger than a high limit and the threshold is larger than a minimum threshold.

33. A capsule camera apparatus, comprising:
a housing adapted to be swallowed;
a light source within the housing;
a camera within the housing for capturing a first digital image and a second digital image of a scene illuminated by the light source;
a motion detector within the housing comprising:
　a metric measurement module coupled to the first digital image and the second digital image measures a metric of a motion between the first digital image and the second digital image;
　a motion detection module coupled to the metric measurement module detects the motion based on the metric and a threshold; and
　a threshold update module coupled to the metric measurement module and the motion detection module updates the threshold;
a wireless transmitter within the housing coupled to transmit the second digital image; and
a control circuit within the housing that designates the second digital image for transmission via the wireless transmitter based on the motion detected by the motion detection module.

34. A capsule camera apparatus, comprising:
a housing adapted to be swallowed;
a light source within the housing;
a light control circuitry coupled to the light source to provide light control signal;
an archival storage device;
a camera within the housing for capturing a first digital image and a second digital image of a scene illuminated by the light source;
a motion detector within the housing comprising:
　a metric measurement module coupled to the first digital image and the second digital image measures a metric of a motion between the first digital image and the second digital image;
　a motion detection module coupled to the metric measurement module detects the motion based on the metric and a threshold; and
　a threshold update module coupled to the metric measurement module and the motion detection module updates the threshold, wherein the threshold updating is related to the light control signal; and
a control circuit within the housing that designates the second digital image for further processing based on the motion detected by the motion detection module.

35. A capsule camera apparatus, comprising:
a housing adapted to be swallowed;
a light source within the housing;
a light control circuitry coupled to the light source to provide light control signal;
a camera within the housing for capturing a first digital image and a second digital image of a scene illuminated by the light source;
a motion detector within the housing comprising:
　a metric measurement module coupled to the first digital image and the second digital image measures a metric of a motion between the first digital image and the second digital image;
　a motion detection module coupled to the metric measurement module detects the motion based on the metric and a threshold; and a threshold update module coupled to the metric measurement module and the motion detection module updates the threshold, wherein the threshold updating is related to the light control signal; and a wireless transmitter within the housing coupled to transmit the second digital image; and a control circuit within the housing that designates the second digital image for transmission via the wireless transmitter based on the motion detected by the motion detection module.

* * * * *